(12) United States Patent
Kipp et al.

(10) Patent No.: US 8,961,579 B2
(45) Date of Patent: Feb. 24, 2015

(54) PORTABLE PHOTOTHERAPY DEVICE

(75) Inventors: David Jeffrey Kipp, Hudson Falls, NY (US); Jack F. Springer, Jr., Fort Edward, NY (US)

(73) Assignee: Medtek Lighting Corporation, Hudson Falls, NY (US)

( * ) Notice: Subject to any disclaimer, the term of this patent is extended or adjusted under 35 U.S.C. 154(b) by 230 days.

(21) Appl. No.: 12/025,651

(22) Filed: Feb. 4, 2008

(65) Prior Publication Data
US 2008/0255640 A1 Oct. 16, 2008

Related U.S. Application Data

(60) Provisional application No. 60/887,839, filed on Feb. 2, 2007.

(51) Int. Cl.
*A61N 5/06* (2006.01)

(52) U.S. Cl.
CPC ....... *A61N 5/0616* (2013.01); *A61N 2005/0655* (2013.01); *A61N 2005/0661* (2013.01)
USPC ............................................. 607/91; 607/88

(58) Field of Classification Search
USPC ............. 606/2–19; 607/88–94; 362/154, 156, 362/362
See application file for complete search history.

(56) References Cited

U.S. PATENT DOCUMENTS

| | | | |
|---|---|---|---|
| 1,716,603 A * | 6/1929 | Schmidt | 607/91 |
| 2,054,332 A * | 9/1936 | Lower et al. | 607/91 |
| 2,444,379 A * | 6/1948 | Sexton | 607/91 |
| 4,283,661 A | 8/1981 | Doty | |
| 4,444,189 A * | 4/1984 | Seiverd | 607/91 |
| 4,463,413 A | 7/1984 | Shirley | |
| 4,740,707 A * | 4/1988 | Thaw | 607/94 |
| 4,984,571 A * | 1/1991 | Springer et al. | 607/94 |
| 5,149,184 A * | 9/1992 | Hughes et al. | 362/1 |
| 5,377,085 A | 12/1994 | Hermann et al. | |
| 5,446,580 A * | 8/1995 | Collins | 359/350 |
| 5,466,248 A * | 11/1995 | Whitson-Newman | 607/88 |
| 5,919,217 A * | 7/1999 | Hughes | 607/90 |
| 6,273,906 B1 | 8/2001 | Swanson | |
| 6,488,698 B1 * | 12/2002 | Hyman | 607/91 |
| 6,549,809 B2 * | 4/2003 | Ono | 607/100 |
| 6,761,730 B1 * | 7/2004 | Johnson et al. | 607/94 |
| 6,875,225 B1 * | 4/2005 | Pederson et al. | 607/88 |
| 6,942,685 B2 * | 9/2005 | Chapman et al. | 607/91 |
| 7,161,120 B1 | 1/2007 | Stroud et al. | |
| 7,517,101 B2 * | 4/2009 | Tobin | 362/1 |
| 2001/0023363 A1 * | 9/2001 | Harth et al. | 607/90 |
| 2003/0088296 A1 | 5/2003 | Waldmann | |
| 2003/0088297 A1 * | 5/2003 | Stoppler | 607/94 |
| 2005/0159795 A1 | 7/2005 | Savage et al. | |

OTHER PUBLICATIONS

ISR/WO for PCT/US 2008/052967, Medtek Lighting Corp.

* cited by examiner

*Primary Examiner* — Lynsey Crandall
(74) *Attorney, Agent, or Firm* — Baker Botts L.L.P.

(57) ABSTRACT

Disclosed herein is a portable device suited to treating psoriasis and other skin diseases in patients. The device can be carried like a suitcase from one location to another and can be used to treat various body parts, such as the hands, feet, face, and chest. The device includes a carrying case, ultraviolet bulbs, a ballast, and electrical components. The device can also include a timer to measure the duration of the phototherapy treatment.

17 Claims, 3 Drawing Sheets

PORTABLE PHOTOTHERAPY DEVICE

CROSS-REFERENCE TO RELATED APPLICATIONS

This application is claims priority to U.S. Provisional Application Ser. No. 60/887,839, filed Feb. 2, 2007, which is hereby incorporated by reference in its entirety herein.

TECHNICAL FIELD

The present invention relates generally to phototherapy systems and more specifically to a portable phototherapy system.

BACKGROUND

Contemporary hand and foot phototherapy devices are not easily transported because they are often designed without regard to minimizing size or weight. In addition, these devices are often designed to treat a single body part, thus requiring multiple units to treat multiple body parts.

SUMMARY OF THE INVENTION

The present invention provides a portable device suited to treating psoriasis and other skin diseases in patients. The device can be carried like a suitcase from one location to another and can be used to treat various body parts, such as the hands, feet, face, and chest.

The device includes a carrying case, ultraviolet bulbs, a ballast, and electrical components. The device can also include a timer to measure the duration of the phototherapy treatment.

The carrying case includes a base portion and a cover, which are connected by a hinge on the back of the device. The ultraviolet bulbs, ballast, and electrical components are disposed in the base portion. Two panels located on the sides of the case can be used hold the cover up at an angle to allow hands or feet to be inserted into the case and treated therein.

A protective sheet can be used to prevent leakage of ultraviolet light when the device is in the open position. The protective sheet, which has openings to allow hands or feet to be inserted and treated, can be easily attached or detached with the use of fasteners on the top and bottom of the case. After treatment, the protective sheet can be folded up and stored inside the carrying case.

BRIEF DESCRIPTION OF THE DRAWINGS

Further features and advantages of the disclosed subject matter will become apparent from the following detailed description taken in conjunction with the accompanying figures showing illustrative embodiments of the disclosed subject matter, in which.

DETAILED DESCRIPTION

Figure 1:
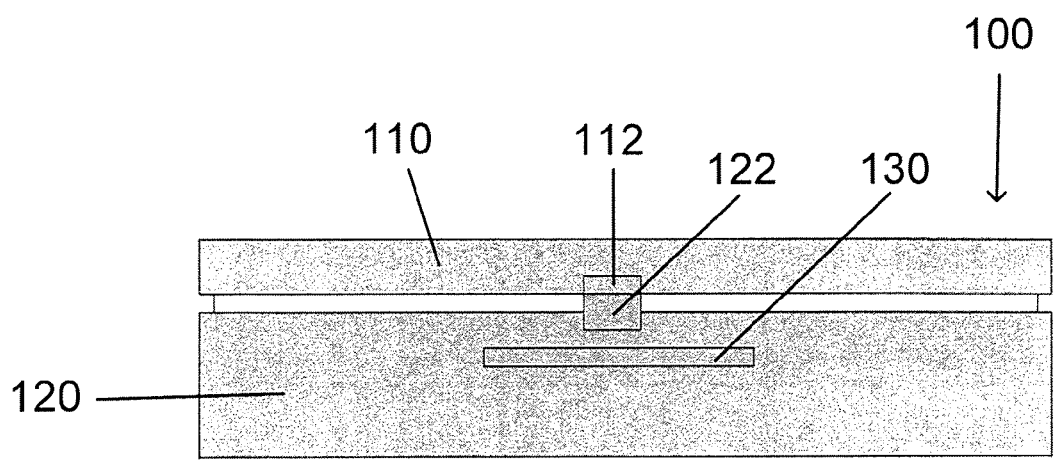
FIG. 1 is a front view of one embodiment of the disclosed subject matter.
Figure 2:
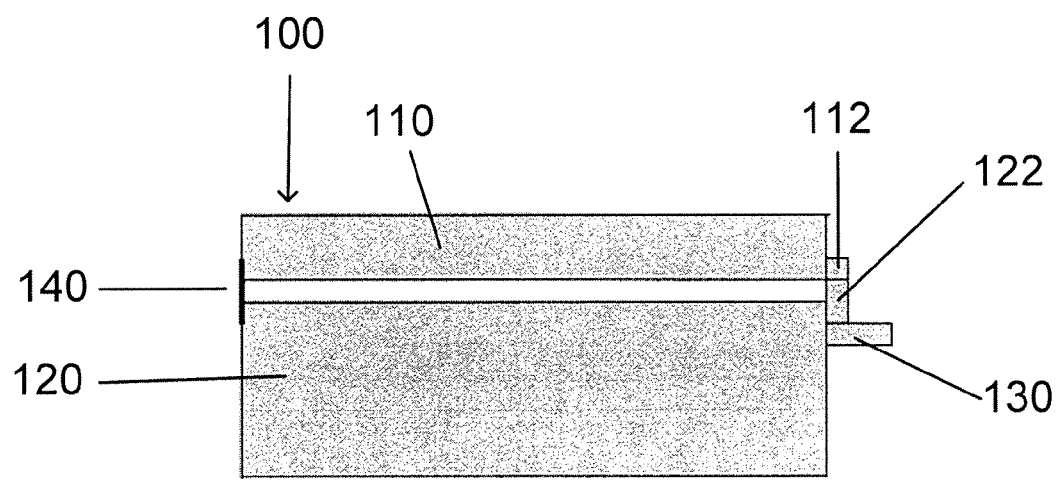
FIG. 2 is an end view of the embodiment depicted in FIG. 1.
Figure 3:
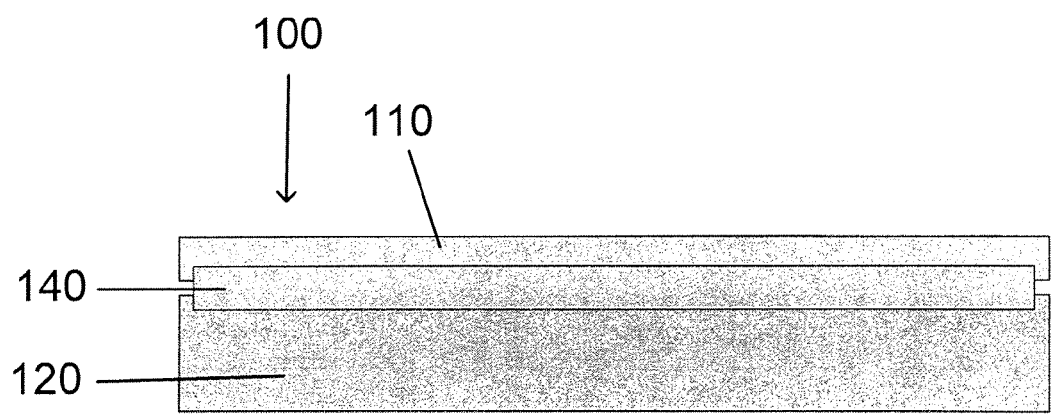
FIG. 3 is a back view of the embodiment depicted in FIG. 1.
Figure 4:
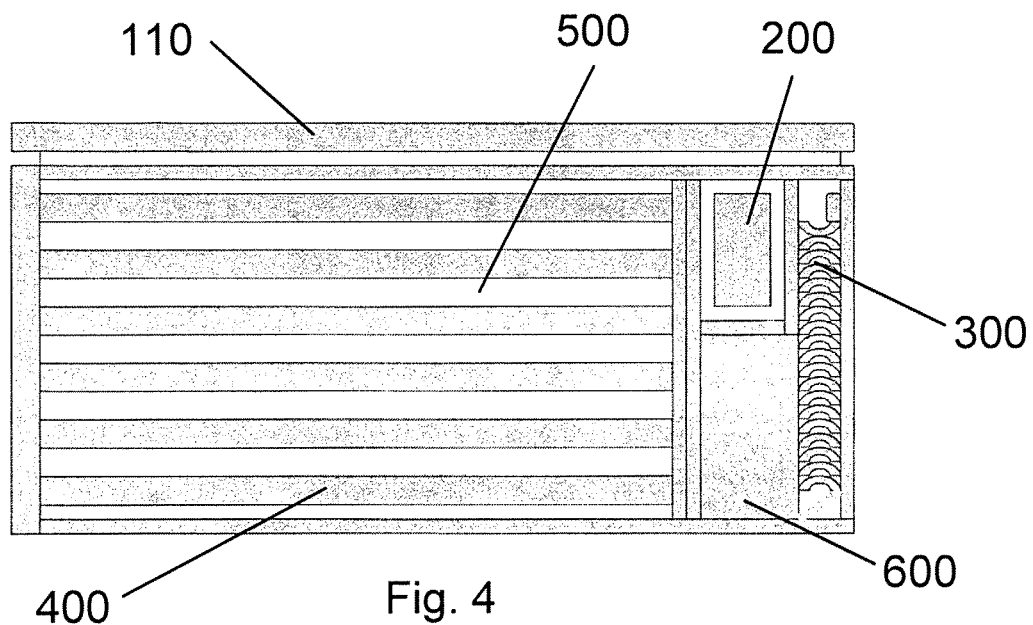
FIG. 4 is a top view of the embodiment depicted in FIG. 1 in an open position.

In one embodiment, as shown in FIGS. 1-4, the portable phototherapy device 10 includes a carrying case 100, ultraviolet bulbs 400, a ballast 500, and electrical components 600. The carrying case can be suitcase-sized. Preferably, the carrying case is approximately 34.5 inches wide, 16 inches deep, and 5 inches high, but the width can range from 12 inches to 52 inches, the depth can range from 6 inches to 34 inches, and the height can range from 2 inches to 23 inches.

According to one embodiment, the carrying case 100 includes a base portion 120 and a cover 110, which are connected to each other by a hinge 140 or other connector disposed on the back of the device. Preferably, the cover 110 is approximately 1.5 inches high, but the height can range from 1/16 inch to 6 inches. The ultraviolet bulbs 400, ballast 500, and electrical components 300 are disposed in the base portion 120. The ultraviolet bulbs 400 are disposed in the top of the base portion 120 so that they shine directly onto body parts inserted into the device. The ultraviolet bulbs 400 can be covered with shielding made of acrylic or other material. Body parts that cannot be inserted into the device 10, such as the face and chest, can be treated by shining light emitted from the open device 10 onto the area requiring treatment.

When not in use, the carrying case 100 can be held closed by a top clasp 112 that engages a bottom clasp 122. A handle 130 can be included on the front of the base 120 for ease of carrying. Preferably, the handle extends from the carrying case 100 by approximately 1.5 inches.

Figure 5:
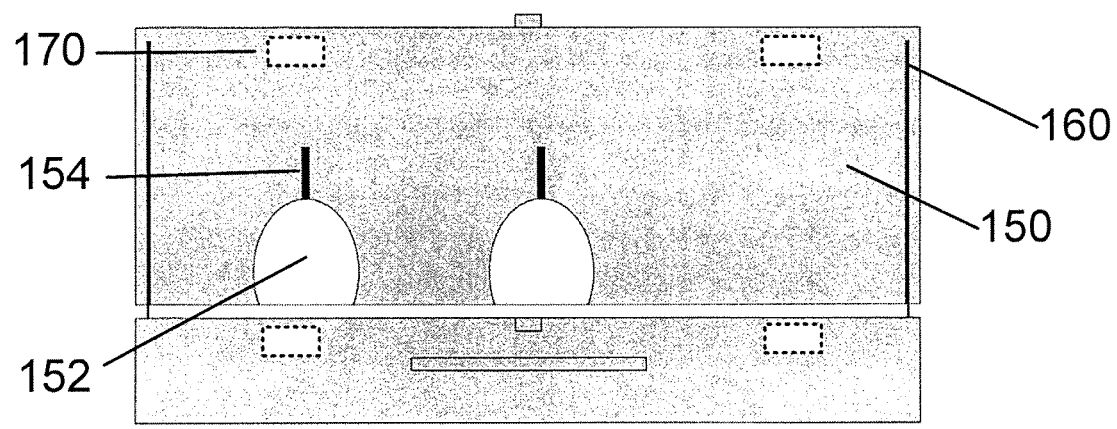
FIG. 5 is a front view of one embodiment of the disclosed subject matter in an open position with a protective sheet in place.
Figure 6:
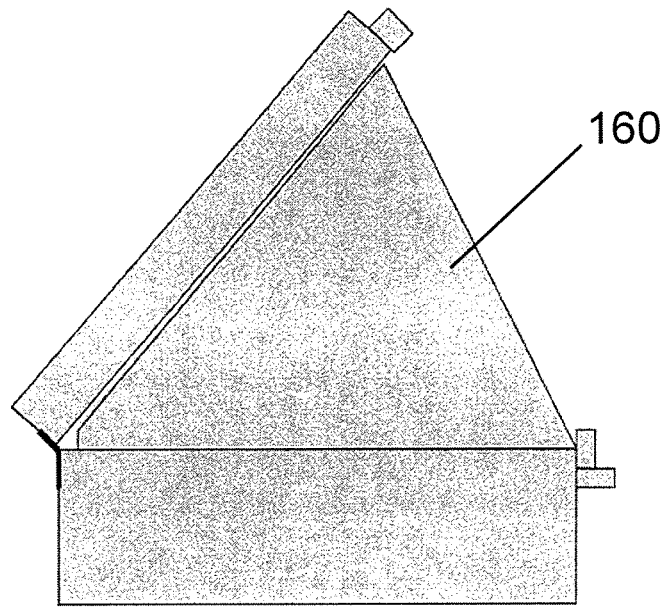
FIG. 6 is an end view of one embodiment of the disclosed subject matter in an open position.

As shown in FIGS. 5-6, panels 160 located on the sides of the carrying case 100 can be used to hold the cover 110 up at an angle to allow body parts to be inserted into the carrying case 100 and treated therein. Preferably, the device reaches a height of approximately 18 inches when the panels are fully extended, but the height can range from 5 inches to 36 inches. The panels 160 can be hinged to fold inside the carry case 100 when it is closed.

According to one embodiment, a protective sheet 150 can be used to prevent leakage of ultraviolet light when the device is in the open position. Preferably, the protective sheet 150 is made of vinyl, but rubber, canvas, leather, plastic, or other materials may be used. The protective sheet 150 rests on the front edges of two side panels 160. The protective sheet 150 has openings 152 to allow hands, feet, or other body parts to be snugly inserted and treated. The openings 152 can feature slits 154 to allow the openings 152 to expand while still preventing leakage of ultraviolet light. After treatment, the protective sheet 150 can be folded up and stored inside the carrying case 100.

According to another embodiment, the protective sheet 150 can be easily attached or detached with the use of fasteners 170 on the top and bottom of the carrying case 100. Preferably, the fasteners are Velcro™ (hook and loop fasteners) or other removable-reattachable strips, but snaps or other fasteners may also be used.

According to another embodiment, the device includes a timer 200 to measure the duration of the phototherapy treatment. In one embodiment of the invention, the timer 200 can be removed from the carrying case 100 and held in the hand.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

The invention claimed is:

1. A portable phototherapy device for selectively treating skin on one or more body parts, comprising:
   a carrying case comprising a base, a cover and a back portion, the carrying case adapted to receive said one or more body parts;
   at least one side panel located on a side of said carrying case that is configured to be folded inside said carrying case when the portable phototherapy device is in a closed position, said at least one side panel configured to engage with the cover such that the cover is oriented upward at an angle to allow a hand or a foot to be inserted into the carrying case;
   a protective sheet attached to the carrying case via fasteners to prevent leakage of ultraviolet light when the portable phototherapy device is in an open position, configured to be folded and stored inside the carrying case when the portable phototherapy device is in the closed position, the protective sheet having openings to allow the hand or foot to be inserted into the carrying case when in the open position; and
   at least one ultraviolet source disposed in said carrying case, said at least one ultraviolet source positioned to treat skin on said one or more body parts with ultraviolet light.

2. The portable phototherapy device of claim 1, further comprising at least one electrical component.

3. The portable phototherapy device of claim 2, further comprising shielding disposed over said at least one ultraviolet source so as to contain said at least one ultraviolet source within said carrying case.

4. The portable phototherapy device of claim 2, wherein said shielding is made of acrylic.

5. The portable phototherapy device of claim 1, wherein said side panel is hinged.

6. The portable phototherapy device of claim 1, wherein said carrying case further comprises a first clasp on a cover and a second clasp on said base that may be engaged to hold said carrying case closed.

7. The portable phototherapy device of claim wherein said carrying case further comprises a handle.

8. The portable phototherapy device of claim 1, wherein said one or more body part openings comprise an expandable portion to allow said one or more body part openings to expand.

9. The portable phototherapy device of claim 1, wherein said protective sheet rests on a front edge of said at least one side panel so as to reduce leakage of ultraviolet light when said portable phototherapy device is in the open position.

10. The portable phototherapy device of claim 1, wherein said protective sheet is attached to said base portion and said cover with fasteners.

11. The portable phototherapy device of claim 10, wherein said fasteners are removable-attachable strips.

12. The portable phototherapy device of claim 11, wherein said removable-attachable strips are hook and loop fasteners.

13. The portable phototherapy device of claim 1, wherein said protective sheet is made of a material selected from the group consisting of vinyl, rubber, canvas, leather, and plastic.

14. The portable phototherapy device of claim 2, further comprising a ballast.

15. The portable phototherapy device of claim 14, further comprising a timer.

16. The portable phototherapy device of claim 15, wherein said timer may be held in the hand.

17. The portable phototherapy device of claim 14, wherein said at least one electrical component and said ballast are disposed in said carrying case.

* * * * *